(12) United States Patent
Li et al.

(10) Patent No.: US 7,426,848 B1
(45) Date of Patent: Sep. 23, 2008

(54) GAS COMPOSITION SENSING USING CARBON NANOTUBE ARRAYS

(75) Inventors: Jing Li, San Jose, CA (US); Meyya Meyyappan, San Jose, CA (US)

(73) Assignee: United States of America as Represented by the Administrator of the National Aeronautics and Space Administration, Washington, DC (US)

( * ) Notice: Subject to any disclaimer, the term of this patent is extended or adjusted under 35 U.S.C. 154(b) by 93 days.

(21) Appl. No.: 11/203,576

(22) Filed: Aug. 5, 2005

(51) Int. Cl.
*G01N 7/00* (2006.01)
(52) U.S. Cl. ...................... 73/23.2; 73/31.05
(58) Field of Classification Search ............... 73/23.2, 73/31.05
See application file for complete search history.

(56) References Cited

U.S. PATENT DOCUMENTS

| | | | |
|---|---|---|---|
| 6,905,655 B2 * | 6/2005 | Gabriel et al. | 422/82.01 |
| 6,997,039 B2 * | 2/2006 | Rao et al. | 73/24.06 |
| 7,013,708 B1 * | 3/2006 | Cho et al. | 73/31.05 |
| 7,040,139 B2 * | 5/2006 | Sunshine | 73/23.2 |
| 2002/0117659 A1 * | 8/2002 | Lieber et al. | 257/14 |
| 2004/0258596 A1 * | 12/2004 | Hirano et al. | 423/240 S |

OTHER PUBLICATIONS

Modi, et al., Miniaturized gas ionization sensors using carbon nanotubes, Letters to Nature, 2003, 171-174, 424, Nature Publishing Group.

* cited by examiner

*Primary Examiner*—Hezron Williams
*Assistant Examiner*—Rodney Frank
(74) *Attorney, Agent, or Firm*—John F. Schipper; Robert M. Padilla

(57) ABSTRACT

A method and system for estimating one, two or more unknown components in a gas. A first array of spaced apart carbon nanotubes ("CNTs") is connected to a variable pulse voltage source at a first end of at least one of the CNTs. A second end of the at least one CNT is provided with a relatively sharp tip and is located at a distance within a selected range of a constant voltage plate. A sequence of voltage pulses $\{V(t_n)\}_n$ at times $t=t_n$ ($n=1, \ldots, N1$; $N1 \geq 3$) is applied to the at least one CNT, and a pulse discharge breakdown threshold voltage is estimated for one or more gas components, from an analysis of a curve $I(t_n)$ for current or a curve $e(t_n)$ for electric charge transported from the at least one CNT to the constant voltage plate. Each estimated pulse discharge breakdown threshold voltage is compared with known threshold voltages for candidate gas components to estimate whether at least one candidate gas component is present in the gas. The procedure can be repeated at higher pulse voltages to estimate a pulse discharge breakdown threshold voltage for a second component present in the gas.

17 Claims, 4 Drawing Sheets

GAS COMPOSITION SENSING USING CARBON NANOTUBE ARRAYS

ORIGIN OF THE INVENTION

This invention was made, in part, by one or more employees of the U.S. government. The U.S. government has the right to make, use and/or sell the invention described herein without payment of compensation therefor, including but not limited to payment of royalties.

FIELD OF THE INVENTION

This invention relates to determination of gas composition, using carbon nanotubes to provide pulse voltage discharges.

BACKGROUND OF THE INVENTION

Few sensors are available to detect inert gases. Conventional inert gas analysis tools primarily rely upon infrared (IR) spectroscopy, mass spectroscopy (MS) and/or thermal conductivity measurements. Thermal conductivity sensors are available for fixed and portable instruments, but this technique is not suitable for measuring extremely low levels of a gas (e.g., less than 1 percent by volume resolution), and the technique has difficulties when the target gas has a thermal conductivity close to that of a background gas. For example, measurement of oxygen in air is not feasible, because the two gases have essentially the same thermal conductivity.

IR spectroscopy is often used to measure carbon dioxide in air, or methane in carbon dioxide, as found in sewage digestor and coal gasification plants. This technique is superior to thermal conductivity sensing in accuracy and resolution, but use of IR is more expensive due to the complex optics and signal processing required. A MS-based sensor can be used to detect presence of an inert gas, but this technique is expensive and heavy and time consuming and is not suitable for in situ measurements. Fourier transform IR and MS techniques require bulky, heavy instruments and/or high temperature operation, and consumption of electrical power is very large.

What is needed is a relatively lightweight and small sensor for inert gases that consumes a relatively small amount of power and that provides measurements that are as accurate as the conventional approaches. Preferably, this sensor should be able to detect and identify presence of one, two or more gases, some or all of which may be relatively inert.

SUMMARY OF THE INVENTION

These needs are met by the invention, which provides an electrical discharge sensor that measures a specific gas breakdown voltage associated with each gas present. In one embodiment, a method for practicing the invention includes the following processes: (1) a first array of spaced apart (preferably, substantially uniformly spaced apart) carbon nanotubes ("CNTs") is provided in a closed chamber, at least one CNT in the first array being attached at a first end to a first variable voltage source, and having a relatively sharp CNT tip at a second end of the at least one CNT, where the second end of the at least one CNT in the first array is located at a distance in a range 10–200 μm from a plate having substantially constant voltage (V=V0); (2) a gas, having at least one unknown gas component and having a pressure in a range $10^{-3}$–760 Torr, is provided in the chamber; (3) a first sequence of voltage pulses, having known voltages $V(t_{n1}) \neq V0$, is applied at selected times $t=t_{n1}$ (n1=1, ..., N1) to the at least one of the CNTs in the first array, and a measurement is taken of at least one of a first electrical current $I(t_{n1}; 1)$ and a first accumulated electrical charge $e(t_{n1}; 1)$ that passes between the at least one CNT and the substantially constant voltage plate, for each of at least N1 distinct voltages $V(t_1), V(t_2), \ldots, V(t_{N1})$ (preferably with monotonically increasing magnitudes) at times $t=t_{n1}$, (n1=1, 2, ..., N1), where $N1 \geq 2$ and $\Delta t_{n1+1} - t_{n1}$ is at least equal to a selected gas recovery time; (4) a first pulse discharge breakdown threshold voltage V(1; thr) is estimated from a comparison of at least one of (i) three current values $I(t_{n1-m1}; 1)$, $I(t_{n1}; 1)$ and $I(t_{n1+m2}; 1)$ ($m1 \geq 1$; $m2 \geq 1$) with each other, and (ii) three cumulative electrical charge values $e(t_{n1-m1}; 1)$, $e(t_{n1}; 1)$ and $e(t_{n1+m2}; 1)$ with each other. For example, the slope of the curve I(t; 1) or the curve e(t; 1), extended to continuous values of time t, may abruptly increase or otherwise change as the discharge breakdown threshold, V=V(1; thr) is reached or exceeded.

Two or more CNT arrays, spaced apart from each other, can be pulsed at different voltages $V(t_{n1}; 1) < V(t_{n1+1}; 1) \ldots < V(t_{n1+N}; 1)$ at spaced apart times (i) to determine more quickly the breakdown threshold voltage of an unknown gas component that is present, by bracketing the breakdown threshold voltage, or (ii) to independently determine pulse discharge breakdown threshold voltages for two or more distinct gas components that may be simultaneously present. Because the exposed tips of the CNTs are relatively sharp, (i) the amount of power required at a given voltage level is less than would be required for tips that are blunter and/or broader, and (ii) the pulse discharge breakdown threshold voltage for a given gas can be determined more precisely. The CNTs used here are preferably multi-wall CNTs ("MWCNTs," including two or more concentric, roughly cylindrical layers) and/or carbon nanofibers ("CNFs," including two or more concentric, roughly conical layers).

DESCRIPTION OF BEST MODES OF THE INVENTION

Figure 1:
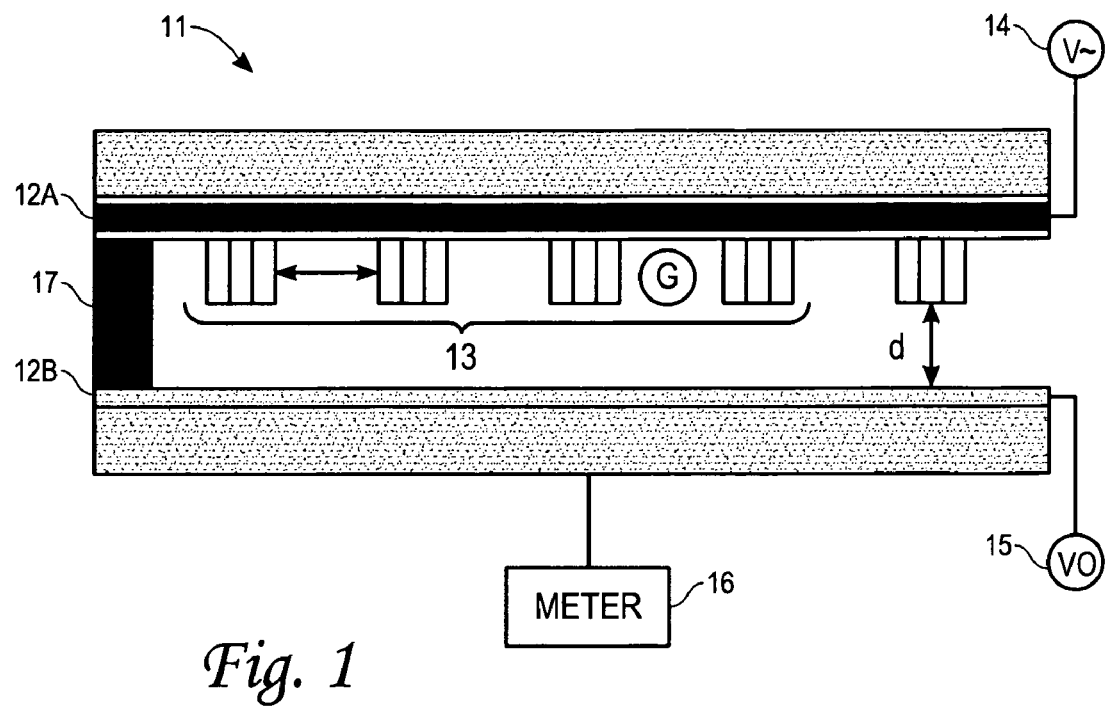
FIGS. 1 and 2 illustrate two systems for practicing the invention, using one array and two independently addressable arrays of CNTs.

FIG. 1 illustrates a system 11 for practice one embodiment of the invention. The system 11 includes first and second plates, 12A and 12B, where the first plate 12A is connected to spaced apart CNTs at a first CNT array end and is connected to a source 14 of variable pulsed voltage; and the second plate 12B is connected to a source 15 of, or is maintained at, substantially constant voltage V0 (which may be, but need not be, zero voltage). For definiteness, it is assumed here that the voltages associated with the first plate 12A are positive; if the voltages of the first plate are negative, V(t) should be replaced by −V(t) in the following discussion.

Figure 2:
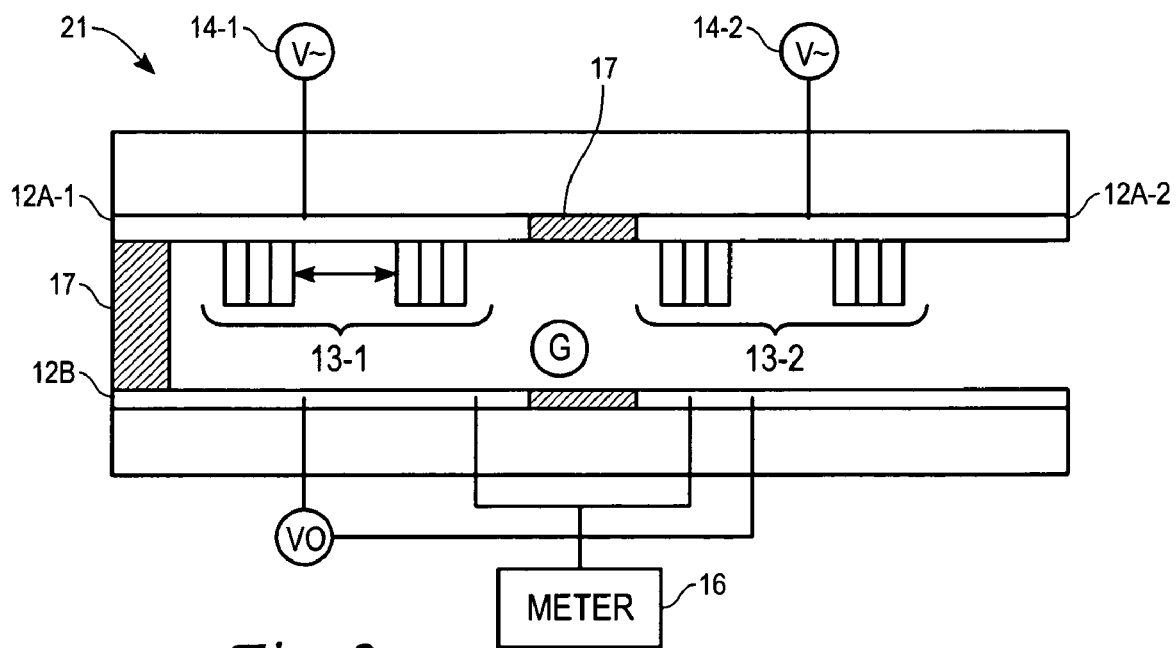

The first plate 12A or the second plate 12B is also connected to a current measurement device 16, for example, an ammeter or a time integrated or cumulative electrical charge meter (referred to collectively herein as a "meter"). Optionally, each of two or more spaced apart CNT arrays may be connected, through a split plate 12A-1 and 12A-2, as illustrated in FIG. 2 (or, optionally, through a single first plate, as in FIG. 1), to the pulsed voltage sources, 14-1 and 14-2, where a voltage pulse of independent and controllable magnitude can be delivered to each of the (split) plates independently. The first and second plates, 12A and 12B, in FIG. 1 are separated by an insulating spacer 17. Similar insulating spacers may be used to electrically isolate the (split) plates 12A-1 and 12A-2 from each other and from the plate 12B in FIG. 2.

In FIG. 1, and similarly in FIG. 2, a gas G of unknown composition is introduced into a region between the CNT array(s) 13 (or the arrays 13-1 and 13-2) and the second plate 12B. A sequence of voltage pulses $\{V(t_{n1}; 1)\}_{n1}$ (spaced apart in time) of increasing magnitude is delivered by the voltage pulse source 14 to the first plate 12A in FIG. 1 ($n1=1, 2, \ldots$ N1). At the voltage $V(n_{n0}; 1)$, no discharge breakdown occurs in the gas, but at the next voltage in the sequence, $V(n_{n0+1}; 1)$, discharge breakdown occurs in the gas. This indicates that the gas discharge breakdown voltage magnitude is greater than $V(t_{n0})$ but is no larger than $V(t_{n0+1})$. This smaller pulse voltage interval, $V(n_{n0}; 1) < V < V(n_{n0}; 1)$, can be further explored by delivering a sequence of voltage pulses with magnitudes increasing from $V(t_{n0}; 1)$ to $V(t_{n0+1}; 1)$, to obtain a finer estimate of the actual pulse discharge breakdown threshold voltage for a first component of the gas. The slope of the curve $I(t; k)$ or $e(t; k)$ ($k=1, 2, \ldots$) abruptly increases as each pulse discharge breakdown threshold voltage $V(k; thr)$ is reached or exceeded. A second component of the gas with a higher pulse discharge breakdown threshold voltage, if present, can be determined in a similar manner, using the system 11 shown in FIG. 1 or using the split plate system 21 shown in FIG. 2.

Presence of pulse discharge breakdown in a gas may be determined in the following manner, using an ammeter or cumulative charging sensing device connected between the first and second plates, 12A and 12B, in FIG. 1. Contemporaneous with delivery of each voltage pulse to the first plate 12A, an electrical current value $I(t; k)$, or a peak electrical current value $I_{peak}(k)$ is measured between the first and second plates, 12A and 12B, Discharge occurs in the gas for delivery of a given voltage pulse if and only if $I(t; k) \geq I(k; thr)$ or $I_{peak}(k) \geq I(k; thr)$ or the slope of the curve $I(t; k)$ abruptly increases, where $I(k; thr)$ is a selected breakdown threshold current value, as illustrated graphically in FIG. 3A. Alternatively, where a cumulative charge sensing device is connected between the first and second plates, 12A and 12B, in FIG. 1, discharge breakdown occurs in the gas for delivery of a given voltage pulse if and only if the time integral $\int I(t; k) dt$, representing cumulative electrical charge $e(t; k)$, for a given time interval including time of delivery of the voltage pulse, is greater than a threshold electrical charge value $e(k; thr)$, or the slope of the curve $e(t; k)$ abruptly increases, as illustrated in FIG. 3B.

Figure 3A:
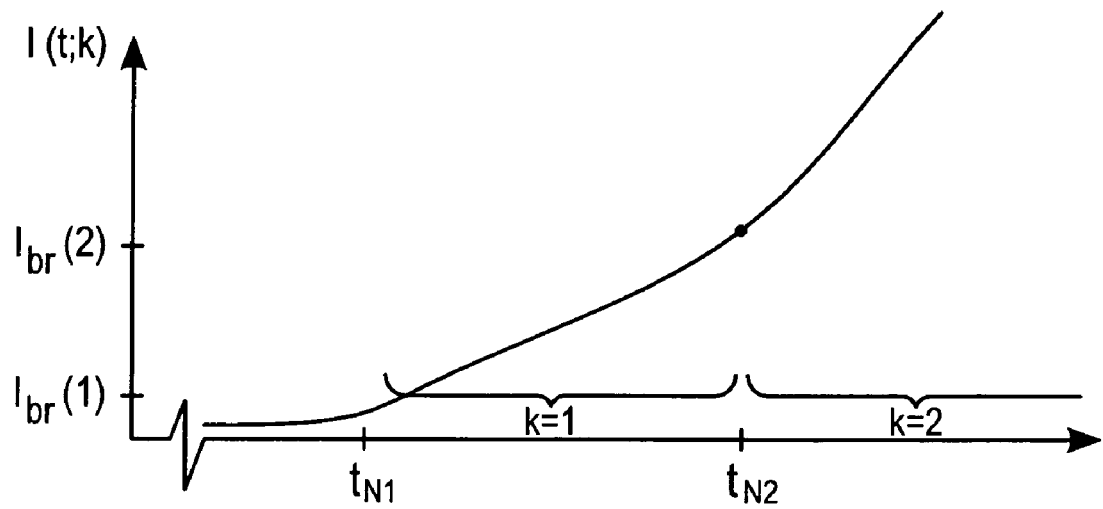
FIGS. 3A and 3B graphically illustrate variation of measured electrical current and cumulative electrical charge, respectively, associated with variation of a pulsed voltage delivered to a CNT array in FIG. 1 or FIG. 2.
Figure 3B:
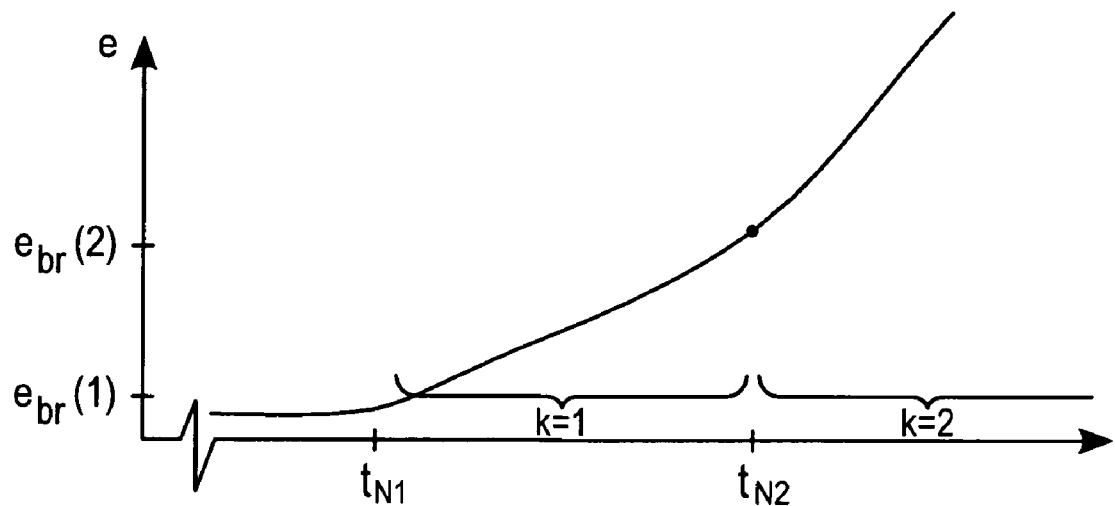

In each of FIGS. 3A and 3B, the measured current $I(t; k)$ and/or the cumulative electrical charge measured $e(t; k)$, respectively, would be expected to continue to increase as the pulse voltage delivered increases beyond the pulse discharge breakdown threshold voltage $V(k; thr)$. If a second gas component is present that has a higher (preferably, substantially higher) associated pulse discharge breakdown threshold voltage, $V(2; thr) > V(1; thr)$, the measured current $I(t; 2)$ or the measured cumulative electrical charge $e(t; 2)$ continues to increase with a certain slope as V increases above $V(1; thr)$ toward, but below, $V(2; thr)$. Above $V=V(2; thr)$, the slope of a curve $I(t_n 2)$ or the slope of a curve $V(t_n; 2)$ abruptly increases, as illustrated in FIGS. 3A and 3B, respectively, indicating presence of a second gas component with a pulse discharge breakdown threshold voltage at $V=V(2; thr) > V(1; thr)$. This second pulse discharge breakdown threshold voltage $V(2; thr)$) is determined in a manner similar to that for the voltage $V(1; thr)$. This approach can be used to estimate a discharge breakdown voltage for two or more gas components, if the pulse discharge breakdown threshold voltages are spaced apart sufficiently.

Figure 4A:
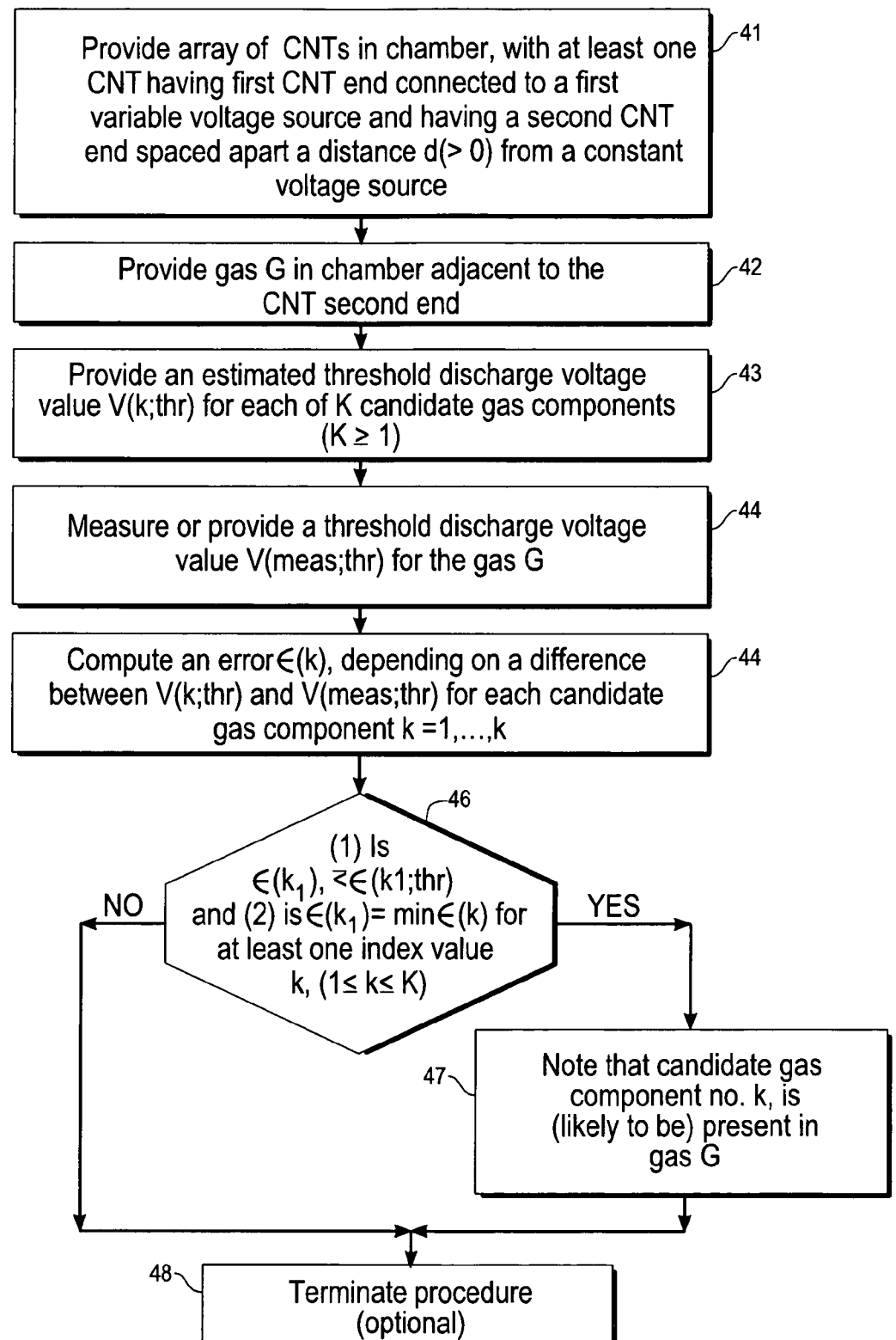
FIGS. 4A/4B are a flow chart of a procedure for practicing the invention.
Figure 4B:
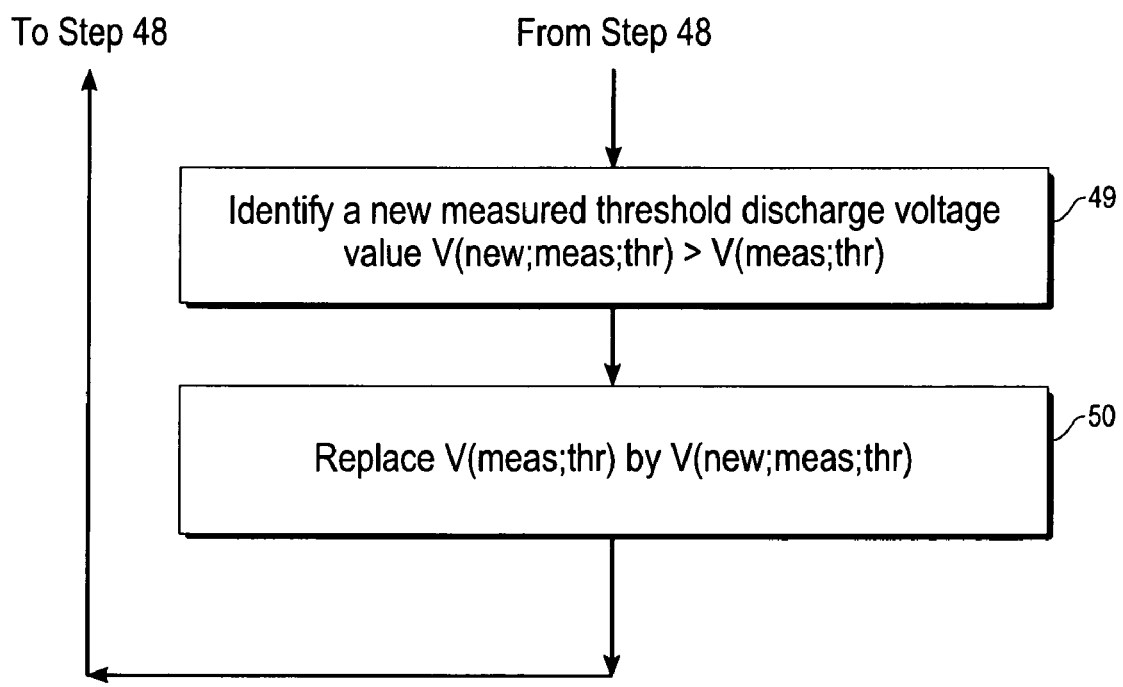

FIGS. 4A/4B is a flow chart of a procedure for estimating a first or nth component of a gas. In step 41, a first array of spaced apart carbon nanotubes ("CNTs") is provided in a closed chamber, at least one CNT in the first array being attached at a first CNT end to a first variable voltage source and having a relatively sharp CNT tip at a second end of the at least one CNT, where the second end of the at least one CNT in the first array is located at a distance in a range 10–200 μm from a substantially constant voltage plate. Each CNT array preferably has a diameter of at least 20 μm, more preferably in a range of 20–50 μm. The array diameter may be as small as 1–5 μm, or smaller if desired. Any two CNT arrays are preferably spaced apart by a distance of at least 200 μm, preferably at least 500 μm. In step 42, having a least one unknown gas component and having a pressure in a range of $10^{-3}$–760 Torr, is provided in the chamber.

In step 43, an (estimated) threshold discharge voltage value $V(k; thr)$ ($k=1, \ldots, K$) is provided for each of K candidate gas components; identified, for example, by use of a slope change method such as illustrated in FIGS. 3A/3B.

In step 44, a threshold discharge voltage value $V(meas; thr)$ is measured or otherwise provided for at least one component of the gas G. In step 45, errors $\epsilon(k)$ including difference values are computed, for example.

$$\epsilon(k) = A \cdot |V(meas; thr) - V(k; thr)|, \tag{1}$$

for each candidate gas component no. $k=1, \ldots, K$, where A is a selected positive value.

The system, in step 46, determines if at least one candidate gas component index no. $k=k1$ exists for which (1) $\epsilon(k=k1)$ is no greater than a threshold error number $\epsilon(k1; thr)$, which may depend upon the index value k1 and/or (2) $\epsilon(k=k1) \leq \epsilon(k)$ for all other values of k. If the answer to the query in step 46 is "yes," the system notes, in step 47, that at least one candidate gas component, no. $k=k1$, is (likely to be) present in the gas G, and moves to step 48, where the procedure is optionally terminated. If the answer to the query in step 46 is "no," the system moves directly to step 48.

Where another (unknown) gas component is present, or believed to be present, in the gas G, with a measured value $V(new; meas; thr) > V(meas; thr)$, the procedure is preferably not terminated in step 48. Presence of the new component may be sensed by determining a new threshold discharge voltage value $V=V(new; meas; thr)$, for example, at which the slope $b(n)$ in FIGS. 3A/3B changes substantially to a new slope $b(n+1) > b(n)$), according to Eq. (3), in step 49. In step 50, the value $V(meas; thr)$ is replaced by the value $V(new; meas; thr)$, and steps 43–48 are reapplied to determine if another candidate gas component is (likely to be) present in the gas G.

The CNT-based gas sensor disclosed here uses the sharp (low radius of curvature) tip(s) of one or more CNTs, preferably multiwall carbon nanotubes ("MWCNTs") or carbon nanofibers ("CNFs"), to generate high strength electrical fields adjacent to the tip(s) for breakdown of gas components with lower voltage application and generation of high leakage current. The system and associated method can provide a high sensitivity, low power consumption tool that is very specific for identification of one or more gas components. A current meter can be multiplexed to measure the leakage current from each of two or more spaced apart CNT arrays, and the pulse voltage delivered can be multiplexed to different CNT arrays to provide different discharge voltages to each array. The current measured in each sensing channel can be digitized to correlate with each of the components of a complex gas. The discharge gas sensor system disclosed here can identify one or more specific discharge breakdown threshold voltages independently of the gas concentration.

The gas sensor disclosed here can be operated at room temperature, or at any other reasonable temperature, and at any reasonable temperature, such as atmospheric pressure or moderately lower. Where the gas pressure in the chamber is p and the tip-to-constant voltage plate distance is d, the product pd will approximately characterize the pulse breakdown threshold voltage where d is no more than 1–3 mean free paths at the gas concentration provided. For example, where an iron cathode is provided, helium, argon and air require minimum pulse voltages of 150 V, 265 V and 330 V, respectively, at pd product values of 2.5 Torr-cm, 1.5 Torr-cm and 0.57 Torr-cm (A. Von Engel, *Ionized Gases,* 1955, p. 173). The proper distance d should be determined or "tuned" for operation at the pressure p chosen, such as p=1 Torr. One distance range that works, not necessarily optimally, is d=50–100 μm.

Approximate values for pulse discharge breakdown threshold voltages for different gases and gas combinations have been preliminarily estimated, using this approach:

V(1; br)=164 V for He,
V(2; br)=245 V for Ar,
V(3; br)=345 V for air,
V(4; br)=430 V for $NH_3$.

What is claimed is:

1. A method for estimating the composition of a gas, the method comprising:
   providing a first array of spaced apart carbon nanotubes ("CNTs") in a closed chamber, at least one CNT in the first array being attached at a first CNT end to a first variable voltage source and having a relatively sharp CNT tip at a second end of the at least one CNT, where the second end of the at least one CNT in the first array is located at a distance in a range of about 10–200 μm from a substantially constant voltage plate;
   providing a gas, having at least one unknown gas component and having a pressure in a range of about $10^{-3}$–760 Torr, in the chamber;
   applying first voltage pulses, having voltages, $V(t_{n1}; 1) \neq V0$, at a sequence of times $t=t_{n1}$ (n1=1, ..., N1; N1≧3) to the at least one CNT in the first array, and measuring at least one of a first associated electrical current $I(t_{n1};1)$ and a first cumulative electrical charge $e(t_{n1};1)$ that passes between the at least one CNT in the first array and the substantially constant voltage plate, for each of the N1 voltages $V(t_1; 1), V(t_2; 1), \ldots, V(t_{N1}; 1)$; and
   estimating a first measured pulse discharge breakdown threshold voltage V(meas;thr) from a comparison of at least one of (i) three electrical current values $I(t_{n1-m1};1)$, $I(t_{n1};1)$ and $I(t_{n1+m2};1)$ with each other; and (ii) three cumulative electrical charge values $e(t_{n1-m1};1)$, $e(t_{n1};1)$ and $e(t_{n1+m2}; 1)$ with each other, for selected numbers m1≧1 and m2≧1;
   providing a threshold discharge voltage value V(k; thr) for each of K candidate gas components, numbered k=1, ..., K (K≧1);
   computing an error $\epsilon(k)$ (k=1, ..., K) that depends upon a difference between the measured breakdown threshold voltage V(meas; thr) and the threshold discharge voltage value V(k; thr);
   when the error $\epsilon(k)$, for k=k1, satisfies at least one of the conditions (1) $\epsilon(k1) \leq e(k1;thr)$, where $\epsilon(k1;thr)$ is a selected threshold error, and (2) $e(k1;thr) \leq \min_{1 \leq k \leq K} \epsilon(k)$, interpreting this satisfaction as indicating that the gas component no. k=k1 is likely to be present in the gas G; and
   when no candidate gas component no. k=k1, exists that satisfies at least one of the conditions (1) $\epsilon(k1) \leq \epsilon(k1; thr)$ and (2) $e(k1;thr) \leq \min_{1 \leq k \leq K} \epsilon(k)$, interpreting this satisfaction as indicating that none of the gas components no. k=1, ..., K is likely to be present in the gas G.

2. The method of claim 1, further comprising:
   when said error $\epsilon(k)$, for k=k1, satisfies both of said conditions (1) $\epsilon(k1) \leq \epsilon(k1; thr)$ and (2) $e(k1;thr) \leq \min_{1 \leq k \leq K} \epsilon(k)$, interpreting this satisfaction as indicating that said gas component no. k=k1 is present in said gas G.

3. The method of claim 1, further comprising choosing said error $\epsilon(k)$ to be $\epsilon(k)=A \cdot |V(meas; thr) - V(k; thr)|$, where A is a selected positive value.

4. The method of claim 1, further comprising:
   providing said sequence $\{V(t_{n1}; 1)\}_n$ of said voltages as a monotonic sequence satisfying $V(t_1; 1) < V(t_{(1)}) < \ldots < V(t_{N1}; 1)$, with $V(t_1; 1)$ less than a breakdown voltage threshold for said gas; and
   interpreting occurrence of the simultaneous conditions (i) $I(t_{n1}; 1) < I(1; thr)$, where I(1;thr) is a selected threshold current value, and (ii) $I(t_{n1-1}; 1) \geq I(1; thr)$ and (iii) $V(t_{n1}; 1) < V(t_{n1+1}; 1)$ as indicating that a component in said gas is present having a pulse discharge breakdown threshold voltage V(1; thr) satisfying $V(t_{n1}; 1) < V(1; thr) \leq V(t_{n1+1}; 1)$.

5. The method of claim 1, further comprising:
   providing said sequence $\{V(t_{n1}; 1)\}_n$ of said voltages as a monotonic sequence satisfying $V(t_1; 1) > V(t_2; 1) > \ldots > V(t_{N1}; 1)$, with $V(t_1; 1)$ greater than a breakdown voltage threshold for said gas; and
   interpreting occurrence of the simultaneous conditions (i) $I(t_{n1}; 1) > I(1; thr)$, where I(1;thr) is a selected threshold current value, and (ii) $I(t_{n1-1}; 1) \leq I(1; thr)$ and (iii) $V(t_{n1}; 1) > V(t_{n1+1}; 1)$ as indicating that a component in said gas is present having a pulse discharge breakdown threshold voltage V(1; thr) satisfying $V(t_{n1}; 1) > V(1; thr) \geq V(t_{n1+1}; 1)$.

6. The method of claim 1, further comprising:
   providing said sequence $\{V(t_{n1}; 1)\}_n$ of said voltages as a monotonic sequence satisfying $V(t_1; 1) < V(t_2;1) < \ldots < V(t_{N1}; 1)$; and
   interpreting occurrence of the simultaneous conditions (i) $e(t_n; 1) < e(1; thr)$, where e(1;thr) is a selected threshold electrical charge value, and (ii) $e(t_{n-1}) \geq e(1; thr)$ and (iii) $V(t_{n1}; 1) < V(t_{n1+1}; 1)$ as indicating that a component in said gas is present having a breakdown voltage V(1; thr) satisfying $V(t_{n1}) < V(1; thr) \leq V(t_{n1+1}; 1)$.

7. The method of claim 1, further comprising:
   providing said sequence $\{V(t_{n1}; 1)\}_n$ of said voltages as a monotonic sequence satisfying $V(t_1; 1) > V(t_2;1)) > \ldots > V(t_{N1}; 1)$; and
   interpreting occurrence of the simultaneous conditions (i) $e(t_n; 1) > e(1; thr)$, where e(1;thr) is a selected threshold electrical charge value, and (ii) $e(t_{n-1}) \geq e(1; thr)$ and (iii) $V(t_{n1}; 1) > V(t_{n1+1}; 1)$ as indicating that a component in said gas is present having a breakdown voltage V(1; thr) satisfying $V(t_{n+11}) < V(1; thr) \leq V(t_{n1}; 1)$.

8. The method of claim 1, further comprising:
   providing a second spaced apart array of CNTs in said chamber, each CNT in the second array being attached at a first end to said variable voltage source and having a relatively sharp CNT tip at a second end that is directed toward said constant voltage plate, where the second end of at least one CNT in the second array is located at a distance in a range of about 10–200 μm from said plate, to provide a second pulse voltage that is independent of said first pulse voltage provided by said variable voltage source, and where the second CNT array is spaced apart from the first CNT array by a distance of at least 50 μm; and applying second voltage pulses, having known voltages, $V'(t_{n2}) \neq V0$, at a sequence of times $t=t_{n2}$ ($n2=N1+1, \ldots, N2$; $n2 \geq N1+3$) to the at least one CNT in the second array, and measuring at least one of a second associated electrical current $I'(t_{n2}; 2)$ and a second cumulative electrical charge $e'(t_{n2}; 2)$ that passes between the at least one CNT in the second array and said substantially constant voltage plate, for each of at least N2 voltages $\{V'(t_{n2}; 2)\}_{n2}$; and estimating a second pulse discharge breakdown threshold voltage $V(2; thr)$ from a comparison of at least one of (i) three current values $I'(t_{n2-m3}; 2)$, $I'(t_{n2}; 2)$ and $I'(t_{n2+m4}; 2)$ with each other, and (ii) three cumulative electrical charge values $e'(t_{n2-m3}; 2)$, $e'(t_{n2}2)$ and $e'('_{n2+m4}; 2)$ with each other, where $m3 \geq 1$ and $m4 \geq 1$.

9. A system for estimating the composition of a gas, the system comprising:

a first array of spaced apart carbon nanotubes ("CNTs") in a closed chamber, at least one CNT in the first array being attached at a first CNT end to a first variable voltage source and having a relatively sharp CNT tip at a second end of the at least one CNT, where the second end of the at least one CNT in the first array is located at a distance in a range of about 10–200 μm from a substantially constant voltage plate, where the chamber is arranged to receive a gas, having at least one unknown component and having a pressure in a range of about $10^{-3}$–760 Torr, in a region between the at least one CNT and the substantially constant voltage plate;

a voltage pulse source, to provide voltages, $V(t_{n1}; 1) \neq V0$, at a sequence of times $t=t_{n1}$ ($n1=1, \ldots, N1$; $N1 \geq 3$) to the at least one CNT in the first array;

at least one of a current meter and a cumulative electrical charge meter (collectively referred to as a "meter"), for measuring at least one of a first associated electrical current $I(t_{n1}; 1)$ and a first associated cumulative electrical charge $e(t_{n1}; 1)$ that passes between the at least one CNT in the first array and the substantially constant voltage plate, for each of the N1 distinct voltages $V(t_1; 1), V(t_2; 1), \ldots, V(t_{N1}; 1)$; and a computer that is programmed;

(i) to estimate a first measured pulse discharge breakdown threshold voltage $V(meas; thr)$ from a comparison of at least one of (i) three electrical current values $I(t_{n1-m1}; 1)$, $I(t_{n1}; 1)$ and $I(t_{n1+m2}; 1)$ with each other, and (ii) three cumulative electrical charge values $e(t_{n1-m1}; 1)$, $e(t_{n1}; 1)$ and $e(t_{n1+m2}; 1)$ with each other, for selected numbers $m1 \geq 1$ and $m2 \geq 1$;

(ii) to provide a threshold discharge voltage value $V(k; thr)$ for each of K candidate gas components, numbered $k=1, \ldots, K$ ($K \geq 1$);

(iii) to compute an error $\epsilon(k)$ ($k=1, \ldots, K$) that depends upon a difference between the measured breakdown threshold voltage $V(meas; thr)$ and the threshold discharge voltage value $V(k; thr)$;

(iv) when the error $\epsilon(k)$, for $k=k1$, satisfies at least one of the conditions (1) $\epsilon(k1) \leq \epsilon(k1; thr)$, where $\epsilon(k1; thr$ is a selected error threshold value, and (2) $e(k1) \leq \min_{1 \leq k \leq K} \epsilon(k)$, to interpret this satisfaction as indicating that the gas component no. $k=k1$ is likely to be present in the gas G; and (v) when no candidate gas component. no. $k=k1$, exists that satisfies at least one of the conditions (1) $\epsilon(k1) \leq \epsilon(k1; thr)$ and (2) $e(k1) \leq \min_{1 \leq k \leq K} \epsilon(k)$, to interpret this satisfaction as indicating that none of the gas components no. $k=1, \ldots, K$ is likely to be present in the gas G.

10. The system of claim 9, wherein said computer is further programmed so that:

when said error $\epsilon(k)$, for $k=k1$, satisfies both of said conditions (1) $\epsilon(k1) \leq \epsilon(k1; thr)$ and (2) $e(k1) \leq \min_{1 \leq k \leq K} \epsilon(k)$, to interpret this satisfaction as indicating that said gas component no. $k=k1$ is present in said gas G.

11. The system of claim 9, wherein said error $\epsilon(k)$ is chosen to be $\epsilon(k)=A \cdot =V(meas; thr)-V(k; thr)|$, where A is a selected positive value.

12. The system of claim 9, wherein said computer is further programmed to estimate a first pulse discharge breakdown threshold voltage $V(1; thr)$ from a comparison of at least one of (i) three electrical current values $I(t_{n1m1}; 1)$, $I(t_{n1}; 1)$ and $I(t_{n1+m2}; 1)$ with each other, and (ii) three cumulative electrical charge values $e(t_{n1-m1}; 1)$, $e(t_{n1}; 1)$ and $e(t_{n1+m2}; 1)$ with each other fort selected numbers $m1 \geq 1$ and $m \geq 1$.

13. The system of claim 12, wherein:

said voltage pulse source provides said sequence $\{V(t_{n1}; 1)\}_n$ of said voltages as a monotonic sequence satisfying $V(t_1; 1) < V(t_{;1)} < \ldots < V(t_{N1}; 1)$, with $V(t_1; 1)$ less than a breakdown voltage threshold for said gas; and said computer is further programmed to interpret occurrence of the simultaneous conditions (i) $I(t_{n1}; 1) < I(1; thr)$, where $I(1;thr)$ is a selected threshold current value, and (ii) $I(t_{n1-1}; 1) \geq I(1; thr)$ and (iii) $V(t_{n1}; 1) < V(t_{n1+1}; 1)$ as indicating that a component in said gas is present having a pulse discharge breakdown threshold voltage $V(1; thr)$ satisfying $V(t_{n1}; 1) < V(1; thr) \leq V(t_{n1+1}; 1)$.

14. The system of claim 9, wherein:

said pulse voltage source provides said sequence $\{V(t_{n1}; 1)\}_n$ of said voltages as a monotonic sequence satisfying $V(t_1; 1) > V(t_2; 1) > \ldots > V(t_{N1}; 1)$, with $V(t_1; 1)$ greater than a breakdown voltage threshold for said gas; and said computer is further programmed to interpret occurrence of the simultaneous conditions (i) $I(t_{n1}; 1) > I(1; thr)$, where $I(1;thr)$ is a selected threshold current value, and (ii) $I(t_{n1-1}; 1) \leq I(1; thr)$ and (iii) $V(t_{n1}; 1) > V(t_{n1+1}; 1)$ as indicating that a component in said gas is present having a pulse discharge breakdown threshold voltage $V(1; thr)$ satisfying $V(t_{n1}; 1) > V(1; thr) \geq V(t_{n1+1}; 1)$.

15. The system of claim 9, wherein:

said voltage pulse source provides said sequence $\{V(t_{n1}; 1)\}_n$ of said voltages as a monotonic sequence satisfying $V(t_1; 1) > V(t_2; 1) > \ldots > V(t_{N1}; 1)$, with $V(t_1; 1)$ greater than a breakdown voltage threshold for said gas; and said computer is further programmed to interpret occurrence of the simultaneous conditions (i) $e(t_n; 1) < e(1;thr)$, where $e(1;thr)$ is a selected threshold electrical charge value, and (ii $e(t_{n=1}) > e(1;thr)$ and (iii) $V(t_{n1}; 1) > V(t_{n1+1}; 1)$ as indicating that a component in said gas is present having a pulse discharge breakdown threshold voltage $V(1; thr)$ satisfying $V(t_{n1}; 1) > V(1; thr) \geq V(t_{n1+1}; 1)$.

16. The system of claim 9, wherein:

said voltage pulse source provides said sequence $\{V(t_{n1}; 1)\}_n$ of said voltages as a monotonic sequence satisfying $V(t_1; 1) < V(t_2; 1) < \ldots < V(t_{N1}; 1)$; and said computer is further programmed to interpret occurrence of the simultaneous conditions (i) $e(t_n; 1) < e(1; thr)$, where $e(1;thr)$ is a selected threshold electrical charge value, and (ii) $e(t_{n=1}) \geqq e(1; thr)$ and (iii) $V(t_{n1}; 1) < V(t_{n1+1}; 1)$ as indicating that a component in said gas is present having a breakdown voltage $V(1; thr)$ satisfying $V(t_{n1}) < V(1; thr) \leqq V(t_{n1+1}; 1)$.

17. The system of claim 9, wherein:

said voltage pulse source further provides a second spaced apart array of CNTs in said chamber, each CNT in the second array being attached at a first end to said variable voltage source and having a relatively sharp CNT tip at a second end that is directed toward said constant voltage plate, where the second end of at least one CNT in the second array is located at a distance in a range of about 10–200 μm from said plate, to provide a second pulse voltage that is independent of said first pulse voltage provided by said variable voltage source, and where the second array is spaced apart from the first array by a distance of at least 50 μm; and said voltage pulse source applies second voltage pulses, having known voltages, $V'(t_{n2}) \neq V0$, at a sequence of times $t=t_{n2}$ (n2=N1+1,..., N2; N2 $\geqq$ N1+3) to the at least one CNT in the second array;

said meter measures at least one of a second associated electrical current $I'(t_{n2}; 2)$ and a second cumulative electrical charge $e'(t_{n2}; 2)$ that passes between the at least one CNT in the second array and said substantially constant voltage plate, for each of at least N2 voltages $\{V'(t_{n2}; 2)\}_{n2}$; and said computer is further programmed to estimate a second pulse discharge breakdown threshold voltage $V(2; thr)$ from a comparison of at least one of (i) three current values $I'(t_{n2-m3}; 2)$, $I'(t_{n2}; 2)$ and $I'(t_{n2+m4}; 2)$ with each other, and (ii) three cumulative electrical charge values $e'(t_{n2-m3}; 2)$, $e'(t_{n2}2)$ and $e'(_{n2+m4}; 2)$ with each other, where $m3 \geqq 1$ and $m4 \geqq 1$.

* * * * *